(12) United States Patent
Oliphant et al.

(10) Patent No.: US 9,322,750 B2
(45) Date of Patent: Apr. 26, 2016

(54) NEEDLE TRAP FOR USE WITH A GAS CHROMATOGRAPH-MASS SPECTROMETER FOR FIELD SAMPLING AND ANALYSIS

(71) Applicant: TORION TECHNOLOGIES, INC., American Fork, UT (US)

(72) Inventors: Joseph L. Oliphant, Highland, UT (US); Nathan Porter, Kaysville, UT (US); Anthony D. Rands, Orem, UT (US)

(73) Assignee: TORION TECHNOLOGIES, INC., American Fork, UT (US)

( * ) Notice: Subject to any disclaimer, the term of this patent is extended or adjusted under 35 U.S.C. 154(b) by 313 days.

(21) Appl. No.: 13/794,144

(22) Filed: Mar. 11, 2013

(65) Prior Publication Data

US 2013/0233054 A1   Sep. 12, 2013

Related U.S. Application Data

(60) Provisional application No. 61/609,120, filed on Mar. 9, 2012.

(51) Int. Cl.
| | |
|---|---|
| *G01N 1/24* | (2006.01) |
| *G01N 1/22* | (2006.01) |
| *G01N 30/12* | (2006.01) |
| *G01N 30/16* | (2006.01) |
| *G01N 30/08* | (2006.01) |

(52) U.S. Cl.
CPC ............... *G01N 1/24* (2013.01); *G01N 1/2214* (2013.01); *G01N 30/12* (2013.01); *G01N 30/16* (2013.01); *G01N 2030/085* (2013.01)

(58) Field of Classification Search
CPC ........................................................ G01N 1/24
USPC ................... 73/864, 864.51, 864.63, 864.64, 73/863.01, 863.23, 864.16, 864.21, 73/864.71, 864.87; 422/83
See application file for complete search history.

(56) References Cited

U.S. PATENT DOCUMENTS

| | | | | |
|---|---|---|---|---|
| 2,916,057 A | * | 12/1959 | Carle | B01J 4/02 141/27 |
| 3,325,062 A | * | 6/1967 | Harris, Sr. | A61M 5/31513 222/386.5 |
| 3,824,859 A | * | 7/1974 | Harris, Sr. | G01N 35/1079 73/864.87 |
| 3,901,413 A | * | 8/1975 | Harris, Sr. | B01L 3/022 222/309 |
| 4,010,648 A | * | 3/1977 | Harris, Sr. | G01N 1/14 141/369 |
| 4,683,212 A | * | 7/1987 | Uffenheimer | G01N 15/1404 137/571 |
| 5,511,433 A | * | 4/1996 | Sabloewski | B01L 3/0224 73/864.14 |
| 5,792,423 A | * | 8/1998 | Markelov | G01N 30/24 422/307 |
| 6,481,301 B2 | * | 11/2002 | Pawliszyn | G01N 1/2214 422/503 |
| 6,482,361 B1 | * | 11/2002 | Suovaniemi | B01L 3/0217 422/525 |
| 7,479,390 B2 | * | 1/2009 | Pawliszyn | G01N 1/40 422/119 |
| 7,645,611 B2 | | 1/2010 | Pawliszyn | |
| 8,322,577 B2 | * | 12/2012 | Pa | G01F 11/027 222/386 |

* cited by examiner

*Primary Examiner* — Hezron E Williams
*Assistant Examiner* — Hoang Nguyen
(74) *Attorney, Agent, or Firm* — Morriss O'Bryant Compagni, PC

(57) ABSTRACT

A system and method for improving operation of a needle trap by changing a flow path through a needle trap to enable a needle to draw a fluid sample into a working end of the needle and out through the side hole, wherein drawing the sample through the side hole eliminates the possibility of a leak through the side hole while drawing a fluid sample into the working end.

9 Claims, 4 Drawing Sheets

NEEDLE TRAP FOR USE WITH A GAS CHROMATOGRAPH-MASS SPECTROMETER FOR FIELD SAMPLING AND ANALYSIS

BACKGROUND OF THE INVENTION

1. Field of the Invention

This invention relates generally to a needle trap for field sampling that can be used to deliver a sample to a gas chromatography/mass spectrometry (GC/MS) system. More specifically, a needle trap that has a side hole may leak when drawing a sample in through the needle. An improved flow path through the needle is obtained when plugging the non-working end of a needle and using the side hole to draw in a fluid sample through the working end of the needle using a vacuum pump, and forcing the sample back out through the working end by applying a pressure to the side hole when delivering a sample to an analyzer.

2. Description of Related Art

There are many devices designed for chemical analysis. One such useful device is a gas chromatography/mass spectrometry (GC/MS) system. The GC/MS system and other similar devices are used in analyzing and identifying compounds. Samples can be delivered to such systems using a needle trap.

BRIEF SUMMARY OF THE INVENTION

In a first embodiment of the present invention, a system and method for improving operation of a needle trap by changing a flow path through a needle trap to enable a needle to draw a fluid sample into a working end of the needle and out through the side hole, wherein drawing the sample through the side hole eliminates the possibility of a leak through the side hole while drawing a fluid sample into the working end.

These and other objects, features, advantages and alternative aspects of the present invention will become apparent to those skilled in the art from a consideration of the following detailed description taken in combination with the accompanying drawings.

DETAILED DESCRIPTION OF THE INVENTION

Reference will now be made to the drawings in which the various elements of the present invention will be given numerical designations and in which the invention will be discussed so as to enable one skilled in the art to make and use the invention. It is to be understood that the following description is only exemplary of the principles of the present invention, and should not be viewed as narrowing the claims which follow.

Stainless steel needles, sized similarly to gas chromatographic injection needles and packed with a sorbent bed, are used for extraction of gaseous samples, followed by thermal desorption into GC systems. All analytes, both freely dissolved in the gas and associated with particulate matter entrained in the sample, are extracted by the devices.

Figure 1:
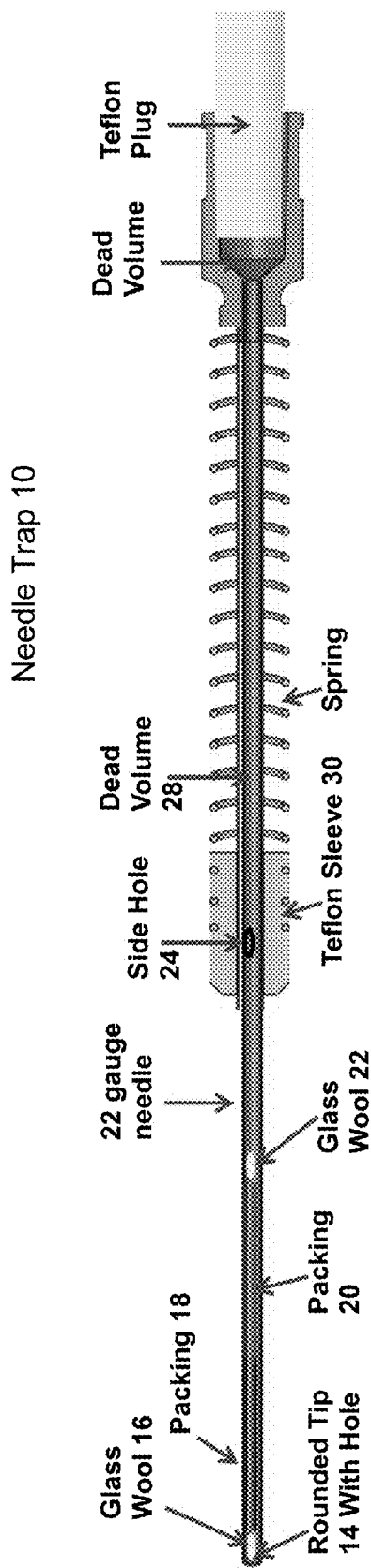
FIG. 1 is a profile cut-away view of a prior art needle trap.
Figure 2:
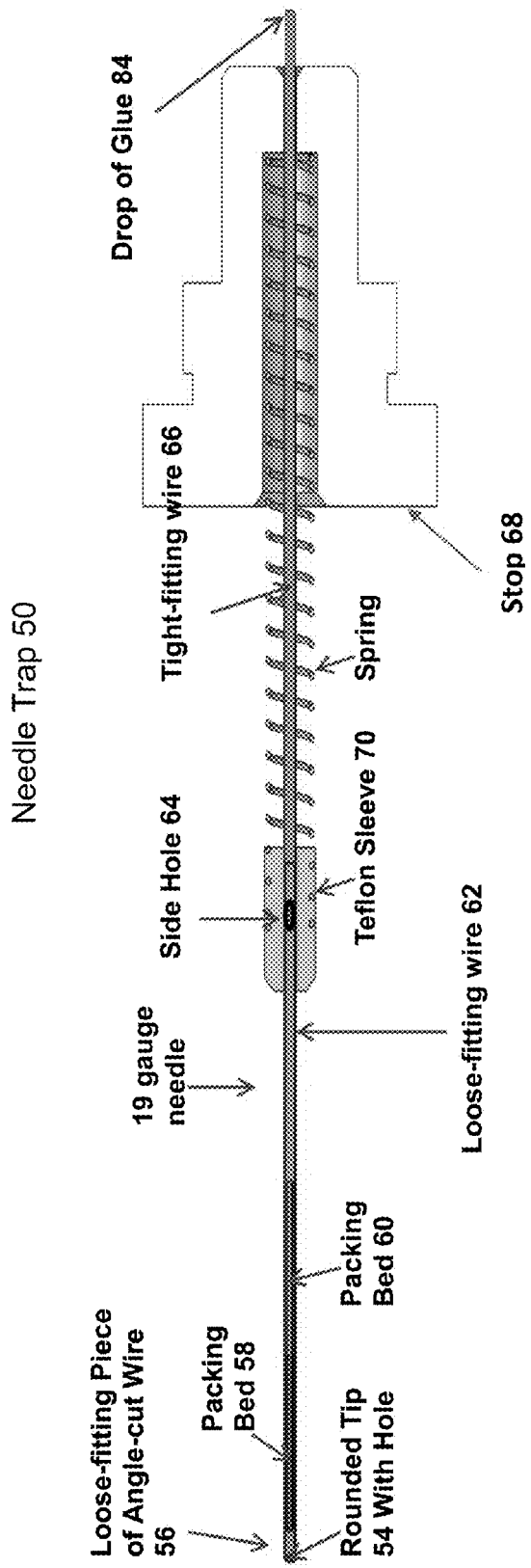
FIG. 2 is a profile cut-away view of a first embodiment of the present invention.

FIG. 1 is a cut-away profile view of a needle trap 10 from the prior art. FIG. 2 is a cut-away profile view of a needle trap 50 of the first embodiment of the present invention.

FIG. 1 shows a needle trap 10 having a needle 12 with a rounded tip 14 at a working end, with glass wool 16 in the rounded tip. A first packing bed 18 is disposed in the needle 12 and adjacent to the glass wool 16. A second packing bed 20 is disposed in the needle 12 and adjacent to the first packing bed 18. Glass wool 22 is disposed in the needle 12 and adjacent to the second bed material 20. The needle 12 then contains an empty volume or dead space 28 until reaching a side hole 24. The needle 12 then continues with the empty volume 28 from the side hole 24 until reaching the end of the needle and a Teflon plug 26.

In contrast, the present invention provides a different needle trap 50 construction in FIG. 2. The needle trap 50 includes a needle 52 with a rounded tip 54 at a working end, with a second loose fitting piece of wire 56 inserted into the rounded tip. The second loose-fitting wire 56 may be cut at an angle. The function of the second loose-fitting wire 56 may be to keep the packing beds 58, 60 from falling out of the needle 52.

A first packing bed 58 is disposed in the needle 52 and adjacent to the second loose-fitting wire 56. A second packing bed 60 is disposed in the needle 52 and adjacent to the first packing bed 58. A second first loose-fitting wire 62 is disposed in the needle 52 and adjacent to the second packing bed 60 until reaching and then passing a side hole 64. A tight-fitting wire 66 is then disposed adjacent to the first loose-fitting wire 62 until passing out of the needle 52 opposite the working end. The function of the tight-fitting wire is to act as a plug that prevents the flow of fluid past the side hole and out of the non-working end of the needle.

It should be understood that the length of the first loose-fitting wire 62 and the tight-fitting wire 66 may vary in relation to the side hole 64. However, it should also be apparent that the first embodiment of FIG. 2 eliminates the dead space 28 of the prior art using the first loose-fitting wire 62 and the tight-fitting wire 66.

Differences between the needle traps 10, 50 include the following aspects. First, the dead space 28 may be defined as the space between the glass wool 22 and the end of the needle at the non-working end in the prior art. This dead space is filled by the first loose-fitting wire 62 and the tight-fitting wire 66 in the present invention.

The needle trap 10 may use a plunger-like device to draw a sample into the needle 12. The side hole 24 is supposed to be sealed by the Teflon sleeve 30, but it may leak.

While the tight-fitting wire 66 does not allow the flow of a gas through the needle 52, the first loose-fitting wire 62 does allow a limited flow of gas. The first loose-fitting wire 62 substantially reduces the volume of the dead space in the first embodiment. It has been observed that when an injection from the needle 52 into an analyzer injection port (shown in FIG. 3) is made, the lack of dead space in the first embodiment of FIG. 2 may cause the GC peaks to come out sharper and cleaner.

Putting a sample into the needle 52 takes place with flow entering through the pointed working end 54 of the needle 52 and out through the side hole 64. In contrast, a needle in the prior art teaches flow in through the pointed end of the needle and out through the other end with the side hole being covered. However, by allowing the side hole 64 to not be covered when taking in the sample, this action eliminates the possibility of a leak through the side hole while pulling sample from the working end.

During sampling there is no way to know if there is a leak from the side hole 64. A leak would result in less or even no sample being drawn into the packing beds 58, 60. Therefore, the present invention uses the side hole 64 as a port. A pump is connected to the side hole 64 while the sample is drawn into the needle 52 from the working end 54. The pump is typically a gas pump that applies a suction force to the side hole 64 in order to draw in a fluid sample through the working end 54 of the needle 52. A Teflon sleeve 70 slides over the side hole 64 when it needs to be covered. The Teflon sleeve is slidingly engaged over the side hole 64 to make it easy to move aside when access to the side-hole is needed.

It is noted that the packing material used in the packing beds 58, 60 is known to those skilled in the art and is not considered to be a novel element of the first embodiment of the present invention.

It should also be understood that there may be more than two packing beds in the needle trap 50. Furthermore, the material in the packing beds may be different form each other.

Figure 3:
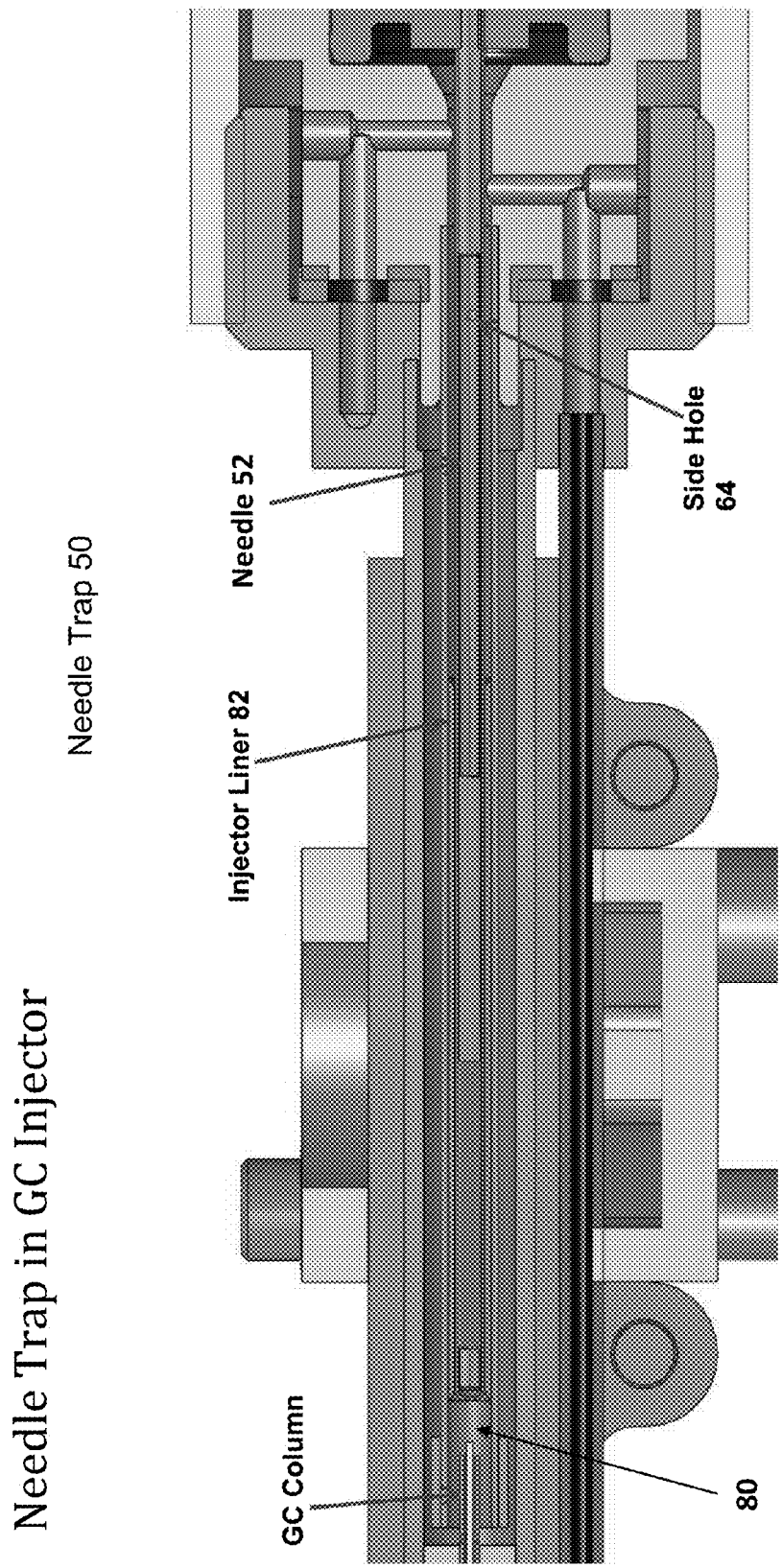
FIG. 3 is a profile cut-away view of the first embodiment of the needle trap in a gas chromatography injector.

In the present invention shown in FIG. 3, the inside diameter of the injection liner 82 fits the outside diameter of the needle 52 leaving a gap of 0.001" or less. This tight fit may cause greater than 95% of the flow of the sample from the needle 52 to go through the needle 52 and not around the needle.

In contrast, the prior art solution to this problem is to have the rounded end of the needle fit tight against an indentation in the liner. The first embodiment is an improvement because it is more robust; little bits of grit or dirt won't cause the delivery system to fail. If the needle 52 is inserted all the way into the injection liner 82, there may be more confidence that the flow is through the needle.

In addition needles of slightly different lengths will still work with the design of the present invention. In contrast, the prior art solution does not allow for automation or using the stop 68 of the needle 52 on top of the injection port to start a run as can be done with the present invention.

The needle trap 50 of the present invention may be a handheld device for taking a sample that is inserted into an analytical device such as a gas chromatography (GC) system or a gas chromatograph/mass spectrometry (GC/MS) system. The needle trap 50 may also be part of an automated device.

The needle 52 that is used to take the sample may be of varying widths. It is preferred that the needle 52 have a diameter that will allow the necessary clearance into an injection port on the desired analytical device.

It is an aspect of the present invention that the needle trap 50 is not part of a syringe-like device having a plunger for drawing a fluid into and out of the needle 52 through both ends. Instead, the end opposite the working end 54 is sealed, and therefore the side-hole 64 becomes a port which is coupled to a pump for drawing the sample to be drawn into the needle 52 and the packing beds 58, 60. As the fluid is drawn into the needle trap 50, particulate matter in the fluid may be trapped in the packing beds 58, 60, and later desorbed in an analytical device.

When it is time to deliver the sample to the analytical device, the present invention avoids the problems associated with a side hole leak. Instead, a gas is delivered to the needle trap 50 through the side hole 64, forcing the sample from the packing beds 58, 60 and into the analytical device. As the needle trap 50 is inserted into the injection liner 82 (see FIG. 3), the Teflon sleeve 70 is pushed back to uncover the side hole 64 so that a fluid can be inserted in order to push the sample into the injector 80. The analytical device is sealed against the stop 68 of the needle trap 50.

It should be understood that fluid may flow around the first loose-fitting wire 62, but not past the tight-fitting wire 66. Thus, when it is time to inject the sample into the analytical device, a gas such as helium is now injected into the side hole 64. It is also noted that the non-working end of the needle trap 50 may be sealed with a drop of glue 84 or any other appropriate seal.

The fluid drawn into the needle trap 50 may be any fluid that is typically delivered to a GC, a GC/MS or any other fluid analyzer.

It is noted that a certain volume of sample is drawn through the packing beds 58, 60 and may be referred to as the breakthrough volume. After a certain volume of a sample is adsorbed into the packing beds 58, 60, the packing beds won't trap anymore and it should start coming out the other end. Calculations performed before experimental data was obtained indicated that the breakthrough volume would be about 100 mL. However, experimental results show that the breakthrough volume obtained was approximately 2 Liters, or 20 times greater than expected. Likewise, calculations showed that a flow rate should be about 10 mL/min, but experimentally, the needle trap 50 has a flow rate of 50 mL/min, or five times greater than expected.

Figure 4:
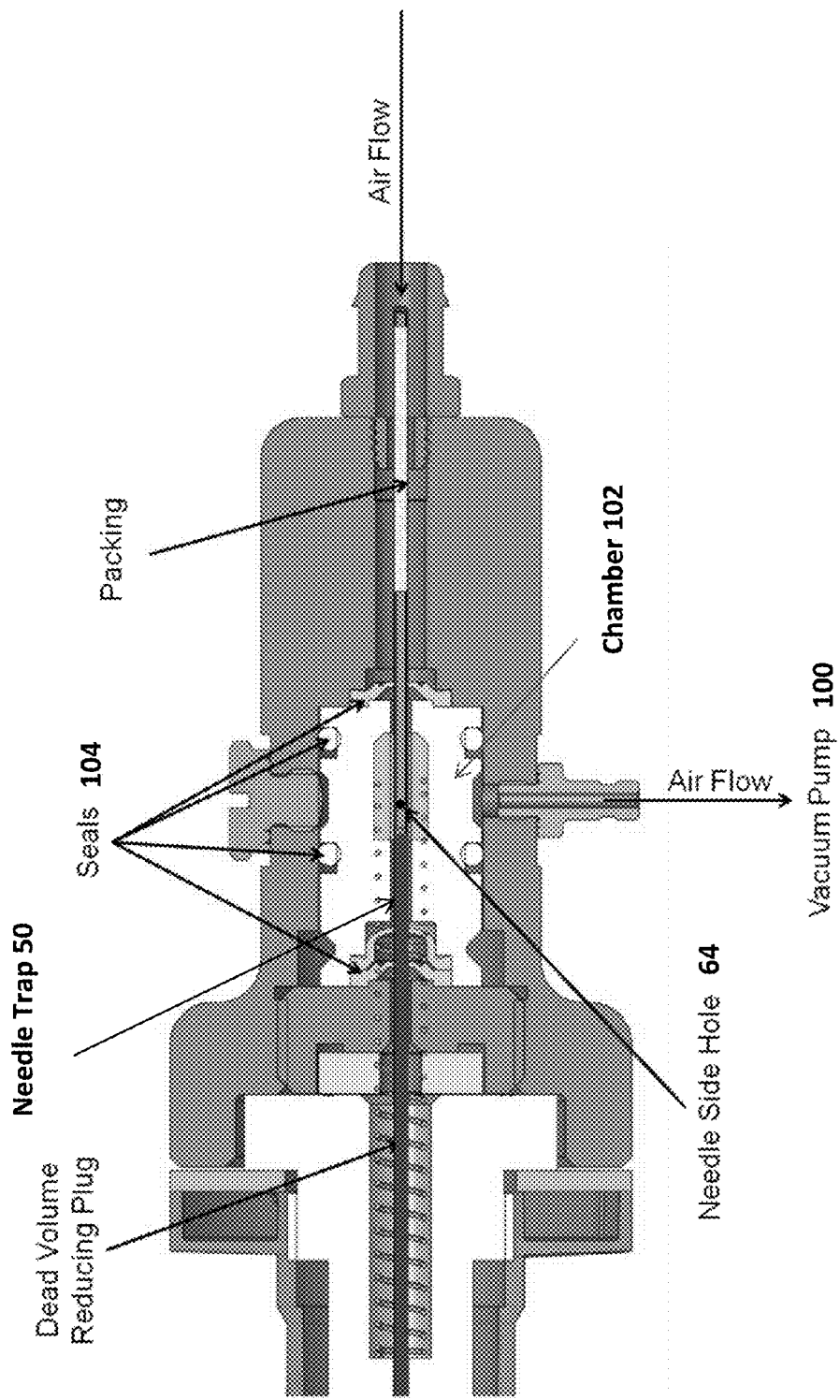
FIG. 4 is a profile cut-away view of the first embodiment of the needle trap prepared to take a fluid sample by applying a suction force to the side hole.

FIG. 4 is provided as a profile cut-away view of the needle trap 50 as it is being prepared to take a fluid sample. As shown, the side hole 64 is exposed on the needle trap 50 by sliding the Teflon sleeve out of the way. The side hole 64 is placed within a chamber 102 in which a vacuum pump 100 can be attached in order to apply a suction force. The chamber 102 includes seals 104 to prevent any leaks.

It is to be understood that the above-described arrangements are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A needle trap system for sampling and delivering a fluid or material in a fluid to an analytical device, said system comprised of:
    a needle having a working end for receiving a sample fluid;
    at least one packing bed disposed in the needle and adjacent to the working end for trapping analyte;
    a side hole disposed through a side of the needle to gain access to an interior space of the needle;
    a first loose-fitting wire disposed in the needle and adjacent to the packing beds at one end to keep the packing beds from moving toward the side hole, and continuing past the side hole; and
    a plug disposed adjacent to the first loose-fitting wire in order to stop fluid flow through the needle past the side hole, and for reducing dead volume within the needle.

2. The needle trap system as defined in claim 1 wherein the system is further comprised of a second loose-fitting wire in the working end for preventing the packing beds from falling out of the needle.

3. The needle trap system as defined in claim 1 wherein the system is further comprised of a sleeve for slidingly covering the side hole.

4. The needle trap system as defined in claim 1 wherein the system is further comprised of a pump that is coupled to the side hole to apply a suction force to draw a fluid sample into the needle through the working end.

5. The needle trap system as defined in claim 1 wherein the system is further comprised of:
   an analyzer having an injection port for receiving the needle of the needle trap system; and
   a pump for coupling to the side hole to apply a pressure to force the fluid sample from the needle trap system through the working end.

6. A method for preventing a side hole leak when using a needle trap system having a side hole in a needle, said method comprising:
   1) providing a needle having a working end for receiving a sample fluid, at least one packing bed disposed in the needle and adjacent to the working end for trapping an analyte, a side hole disposed through a side of the needle to gain access to an interior space of the needle, a first loose-fitting wire disposed in the needle and adjacent to the packing beds at one end to keep the packing beds from moving toward the side hole, and continuing past the side hole, and a first tight-fitting wire disposed adjacent to the first loose-fitting wire in order to stop fluid flow through the needle past the side hole; and
   2) changing a fluid sample flow path through the needle when drawing in a fluid sample by applying a suction force to the side hole when drawing the fluid sample in through the working end of the needle.

7. The method as defined in claim 6 wherein the method further comprises changing a fluid sample flow path through the needle when delivery the fluid sample by applying a pressure force to the side hole when forcing a fluid sample from the working end of the needle.

8. The method as defined in claim 7 wherein the method further comprises reducing a dead volume within the needle using the tight-fitting wire.

9. A method for improving performance of a needle trap, said method comprising:
   1) providing a needle having a working end for receiving a sample fluid, at least one packing bed disposed in the needle and adjacent to the working end for trapping an analyte, a side hole disposed through a side of the needle to gain access to an interior space of the needle, a first loose-fitting wire disposed in the needle and adjacent to the packing beds at one end to keep the packing beds from moving toward the side hole, the loose-fitting wire continuing past the side hole, and a plug disposed adjacent to the first loose-fitting wire in order to stop fluid flow through the needle past the side hole; and
   2) applying a vacuum pump to the side hole to thereby draw a fluid sample in through the working end of the needle.

\* \* \* \* \*